United States Patent [19]

Teranishi et al.

[11] Patent Number: 4,588,729
[45] Date of Patent: May 13, 1986

[54] TREATING CONVULSIONS WITH DIHYDROURACIL DERIVATIVES

[75] Inventors: Masayuki Teranishi; Chikara Murakata, both of Machida; Ikuo Matsukuma, Susono; Katsuichi Shuto; Shunji Ichikawa, both of Shizuoka, all of Japan

[73] Assignee: Kyowa Hakko Kogyo Co., Ltd., Tokyo, Japan

[21] Appl. No.: 734,607

[22] Filed: May 16, 1985

[30] Foreign Application Priority Data

May 16, 1984 [JP] Japan .................. 59-98193

[51] Int. Cl.$^4$ .................................. A61K 31/52
[52] U.S. Cl. ........................................ 514/263
[58] Field of Search ......................... 514/263

[56] References Cited

FOREIGN PATENT DOCUMENTS 55-108858  6/1980  Japan .

Primary Examiner—Stanley J. Friedman
Attorney, Agent, or Firm—Antonelli, Terry & Wands

[57] ABSTRACT

Offered is an anticonvulsive composition which comprises an effective amount of a dihydrouracil derivative represented by the formula:

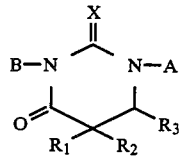

[wherein one of A and B is

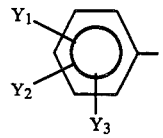

(wherein $Y_1$, $Y_2$ and $Y_3$ are hydrogen atoms, lower alkyl groups, halogen atoms, nitro groups, amino groups, carboxyl groups, lower alkoxycarbonyl groups or trifluoromethyl groups), a naphthyl group or a diphenylmethyl group, and the other is a hydrogen atom, a lower alkyl group, a lower alkenyl group, a cyclopentyl group, a cyclohexyl group or

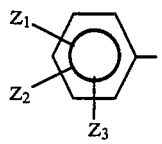

(wherein $Z_1$, $Z_2$ and $Z_3$ are hydrogen atoms, lower alkyl groups, halogen atoms or trifluoromethyl groups), $R_1$, $R_2$ and $R_3$ are hydrogen atoms or lower alkyl groups, and X is an oxygen atom or a sulfur atom] and at least one pharmaceutically acceptable carrier.

14 Claims, No Drawings

TREATING CONVULSIONS WITH DIHYDROURACIL DERIVATIVES

BACKGROUND OF THE INVENTION

The present invention relates to an anticonvulsive agent.

Various anticonvulsive agents are known, for example, phenytoin(diphenylhydantoin), etc.

Now, it has been found that a compound which has so far been known to have a herbicidal activity has an anticonvulsive action.

SUMMARY OF THE INVENTION

The present invention relates to an anticonvulsive composition which comprises an effective amount of a dihydrouracil derivative represented by the formula (I):

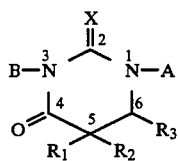

[wherein one of A and B is

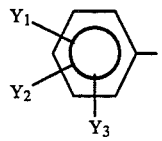

(wherein $Y_1$, $Y_2$ and $Y_3$ are hydrogen atoms, lower alkyl groups, halogen atoms, nitro groups, amino groups, carboxyl groups, lower alkoxycarbonyl groups or trifluoromethyl groups), a naphthyl group or a diphenylmethyl group, and the other is a hydrogen atom, a lower alkyl group, a lower alkenyl group, a cyclopentyl group, a cyclohexyl group or

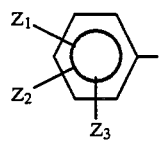

(wherein $Z_1$, $Z_2$ and $Z_3$ are hydrogen atoms, lower alkyl groups, halogen atoms or trifluoromethyl groups), $R_1$, $R_2$ and $R_3$ are hydrogen atoms or lower alkyl groups, and X is an oxygen atom or a sulfur atom] [which will be hereinafter referred to as compound (I)] and at least one pharmaceutically acceptable carrier.

DETAILED DESCRIPTION OF THE INVENTION

In the definitions of $Y_1$, $Y_2$, $Y_3$, $Z_1$, $Z_2$ and $Z_3$ in the formula (I), the lower alkyl groups are straight-chain or branched alkyl groups having 1 to 4 carbon atoms, for example, methyl, ethyl, n-propyl, i-propyl, n-butyl, i-butyl, etc. In the definitions of $Y_1$, $Y_2$, $Y_3$, $Z_1$, $Z_2$ and $Z_3$, the halogen atoms include chlorine, bromine, etc. In the definitions of $Y_1$, $Y_2$ and $Y_3$, the lower alkoxycarbonyl groups are straight-chain or branched alkoxycarbonyl groups having 2 to 7 carbon atoms, for example, methoxycarbonyl, ethoxycarbonyl, etc. In the definition of A and B, the naphthyl group includes both α-naphthyl and β-naphthyl, and the lower alkyl group is a straight-chain or branched alkyl group having 1 to 6 carbon atoms, for example, methyl, ethyl, n-propyl, i-propyl, n-butyl, i-butyl, n-pentyl, n-hexyl, etc. In the definition of A and B, the lower alkenyl group is a straight-chain or branched alkenyl group having 1 to 6 carbon atoms, for example, allyl. In the definitions of $R_1$, $R_2$ and $R_3$, the lower alkyl group is straight-chain or branched alkyl groups having 1 to 3 carbon atoms, namely, methyl, ethyl, n-propyl and i-propyl.

Compound (I) and its process for production thereof are substantially disclosed in Japanese Published Unexamined Patent Application No. 108858/1980.

Preferable examples of compound (I) as an effective component for the anticonvulsive composition of the present invention are shown below:

(1) 1-(2-chlorophenyl)-3-methyl-dihydrouracil (2) 1-(3-chlorophenyl)-3-methyl-dihydrouracil
(3) 1-(4-chlorophenyl)-3-methyl-dihydrouracil
(4) 1-(3,4-dichlorophenyl)-3-methyl-dihydrouracil
(5) 1-(3,4-dichlorophenyl)-3-methyl-2-thio-dihydrouracil
(6) 1-(3,4-dichlorophenyl)-3-ethyl-dihydrouracil
(7) 3-methyl-1-(3-trifluoromethylphenyl)-dihydrouracil
(8) 1-(3-chloro-4-methylphenyl)-3-methyl-dihydrouracil
(9) 1-(2-methyl-4-chlorophenyl)-3-methyl-dihydrouracil
(10) 3-methyl-1-phenyl-dihydrouracil
(11) 3-(3-chlorophenyl)-1-methyl-dihydrouracil
(12) 3-(4-chlorophenyl)-1-methyl-dihydrouracil
(13) 3-(4-chlorophenyl)-1-methyl-2-thio-dihydrouracil
(14) 3-(4-chlorophenyl)-1-ethyl-dihydrouracil
(15) 3-(4-chlorophenyl)-1-isopropyl-dihydrouracil
(16) 3-(4-chlorophenyl)-1-cyclohexyl-dihydrouracil
(17) 1-allyl-3-(4-chlorophenyl)-dihydrouracil
(18) 1-allyl-3-(4-chlorophenyl)-2-thio-dihydrouracil
(19) 3-(4-chlorophenyl)-1,5-dimethyl-dihydrouracil
(20) 3-(4-chlorophenyl)-1,5,5-trimethyl-dihydrouracil
(21) 3-(4-chlorophenyl)-1,6-dimethyl-dihydrouracil
(22) 3-(4-bromophenyl)-1-methyl-dihydrouracil
(23) 1-methyl-3-(4-methylphenyl)-dihydrouracil
(24) 3-(2,5-dichlorophenyl)-1-methyl-dihydrouracil
(25) 3-(3,4-dichlorophenyl)-1-methyl-dihydrouracil
(26) 1-cyclohexyl-3-(3,4-dichlorophenyl)-dihydrouracil
(27) 3-(3,4-dichlorophenyl)-1,5,5-trimethyl-dihydrouracil
(28) 3-(3,4-dichlorophenyl)-1,5-dimethyl-dihydrouracil
(29) 3-(2-chlorophenyl)-1-methyl-dihydrouracil
(30) 1-(2,4-dimethylphenyl)-3-methyl-dihydrouracil
(31) 1-(2,4-dichlorophenyl)-3-methyl-dihydrouracil
(32) 1-(4-chlorophenyl)-dihydrouracil
(33) 3-methyl-1-(4-trifluoromethylphenyl)-dihydrouracil
(34) 3-(2,3-dichlorophenyl)-1-methyl-dihydrouracil
(35) 1-methyl-3-(2-trifluoromethylphenyl)-dihydrouracil
(36) 3-(2,4-dichlorophenyl)-1-methyl-dihydrouracil
(37) 3-(2-chloro-6-methylphenyl)-1-methyl-dihydrouracil
(38) 3-(2-fluorophenyl)-1-methyl-dihydrouracil
(39) 1-(4-chlorophenyl)-3-(2,5-dichlorophenyl)-dihydrouracil
(40) 1-(4-chlorophenyl)-3-(2-chlorophenyl)-dihydrouracil

(41) 1-(4-chlorophenyl)-3-(2-fluorophenyl)-dihydrouracil
(42) 3-methyl-1-(4-nitrophenyl)-dihydrouracil
(43) 1-(4-carboxyphenyl)-3-methyl-dihydrouracil
(44) 1-(4-aminophenyl)-3-methyl-dihydrouracil hydrochloride
(45) 1-methyl-3-(2-nitrophenyl)-dihydrouracil
(46) 3-(2-aminophenyl)-1-methyl-dihydrouracil hydrochloride
(47) 1-methyl-3-α-naphthyl-dihydrouracil
(48) 3-(2-ethoxycarbonylphenyl)-1-methyl-dihydrouracil
(49) 3-diphenylmethyl-1-methyl-dihydrouracil Compound (I) has a low toxicity and a strong anticonvulsive action, which will be obvious from Examples. Above all, the following compounds under compounds (I) have an especially strong anticonvulsive action:

(1) Compounds (I) wherein A is a methyl group, and B is

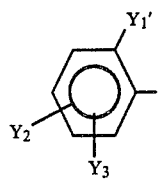

[wherein $Y_1'$ is a halogen atom (especially a chlorine atom), a nitro group, an amino group, a trifluoromethyl group or a lower alkoxycarbonyl group (especially an ethoxycarbonyl group), and $Y_2$ and $Y_3$ have the same meanings as defined in the formula (I)] or a naphthyl group. In the above, compounds wherein 1 $Y_2$ and $Y_3$ are hydrogen atoms, or 2 $Y_1'$ is a halogen atom (especially a chlorine atom), $Y_2$ is a hydrogen atom and $Y_3$ is a halogen atom (especially a chlorine atom) at 3, 4 or 5 positions are especially preferred.

(2) Compounds (I) wherein B is a hydrogen atom or a methyl group, and A is

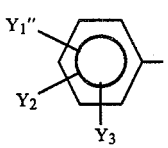

[wherein $Y_1''$ is a trifluoromethyl group at 3-position, or a halogen atom (especially a chlorine atom), an amino group or a trifluoromethyl group at 4-position, and $Y_2$ and $Y_3$ have the same meanings as defined in the formula (I)]. In the above, compounds wherein 1 $Y_2$ and $Y_3$ are hydrogen atoms, or 2 $Y_1''$ is a halogen atoms at 4-position, $Y_2$ is a hydrogen atom and $Y_3$ is a halogen atom (especially a chlorine atom) or a methyl group at 2 or 3 position are especially preferred.

(3) Compounds (I) wherein X is an oxygen atom.
(4) Compounds (I) wherein $R_1$, $R_2$ and $R_3$ are hydrogen atoms.

When compound (I) is used as an anticonvulsive agent, a daily dosage of 100 to 800 mg/60 kg is usually administered wholly at a time, or separately twice or three times.

Tablets, granules, powder, capsules, syrup, injection, etc. prepared in the ordinary manner are used, depending on the administration purpose and administration mode.

For example, when it is used in the form of tablets, it is preferable to use tablets containing 1 to 85% by weight of the active component per tablet. In preparation of tablets, vehicles (for example, lactose, glucose, sucrose, mannitol, light anhydrous silicic acid, etc.), disintegrators (for example, starch, sodium alginate, carboxymethylcellulose calcium, crystalline cellulose, sugar ester, etc.), lubricants (for example, magnesium stearate, talc, etc.), binders (for example, syrup, gelatin solution, polyvinyl alcohol, polyvinylpyrolidone, etc.), dispersing agents (for example, methylcellulose, etc.), plasticizers (for example, glycerin, etc.), coating materials (for example, hydroxypropylcellulose, etc.), pigments, etc. are used according to the ordinary procedure.

The present invention will be described in detail below, referring to Examples.

EXAMPLE 1

Anticonvulsive action

Anticonvulsive action was determined in the following manner:

(1) Maximal electroshock seizure test

Groups of mice, each consisting of 5 male dd-strain mice having a weight of 20±1 g were orally administered with some of said compounds and 60 minutes thereafter, an electric current of 2,000 V, 50 mA was passed to both eyes of the mouse for 0.2 seconds to observe occurrence of tonic extensor. Suppression of tonic extensor occurrence on at least three mice was regarded as effective, and MED (minimum effective dose) for suppressing the convulsion was determined.

(2) Pentetrazol-induced seizure test

Groups of mice, each consisting of 5 male dd-strain mice having a weight of 20±1 g were subcutaneously administered by 120 mg/kg of pentetrazol, and occurrence of clonic seizure was observed. Suppression of clonic seizure occurrence on at least three mice was regarded as effective, and MED was determined.

The results are shown in Table 1.

TABLE 1

| Compound | MED for anticonvulsive action (mg/kg, P.O.) | |
|---|---|---|
| | Maximal electroshock seizure test | Pentetrazol-induced seizure test |
| No. 3 | 75 | 200 |
| 7 | 100 | 100 |
| 24 | 100 | 100 |
| 9 | 150 | 200 |
| 29 | 150 | 150 |
| 34 | 150 | 300 |
| 31 | 100 | 100 |
| 33 | 100 | 300 |
| 36 | 100 | 200 |
| 47 | 100 | 200 |

EXAMPLE 2

Anticonvulsive action (1) Method

The present test was performed in male Carworth Farm mice. All compounds were tested at least 3 dose levels (30, 100, 300 mg/kg) with a fourth dose of 600 mg/kg being performed when there was sufficient quantity available. The vehicles used to solubilize each compound were 30% aqueous polyethylene glycol solution (Compound Nos. 31 to 38, 45, 47 and 48) and 0.9% saline (Compound Nos. 44 and 46).

The following two tests were performed.

MES (Maximum electroconvulsive procedure)

Maximal electroshock seizures were elicited with a 60 cycle alternating current of 50 mA intensity (5–7 times that necessary to elicit minimal electroshock seizures) delivered for 0.2 sec via corneal electrodes. A drop of 0.9% saline was instilled in the eye prior to application of the electrodes in order to prevent the death of the animal. Abolition of the hind limb tonic extension component of the seizure was defined as protection and results were expressed as:

$$\frac{\text{Number of animals protected}}{\text{Number of animals tested}}$$

Sc Met ... Subcutaneous pentylenetetrazole seizure threshold test

First, 85 mg/kg of pentylenetetrazole (produces seizures in greater than 95% of mice) was administered as a 0.5% solution subcutaneously in the posterior midline. The animal was observed for 30 minutes. Failure to observe even a threshold seizure (a single episode of clonic spasms of at least 5 sec duration) was defined as protection and the results were expressed as:

$$\frac{\text{Number of animals protected}}{\text{Number of animals tested}}$$

(2) Evaluation method

All results were classified into one of the following three evaluation standard:

1 Anticonvulsant activity at 100 mg/kg or less
2 Anticonvulsant activity at doses greater than 100 mg/kg, or anticonvulsant activity at 100 mg/kg not reinforced by similar activity at 300 mg/kg
3 No anticonvulsant activity at doses up to and including 300 mg/kg (3) Results are shown in Table 2.

TABLE 2

| Compound No. | Evaluation | Compound No. | Evaluation |
|---|---|---|---|
| 31 | 1 | 38 | 2 |
| 32 | 2 | 44 | 1 |
| 33 | 1 | 45 | 2 |
| 34 | 1 | 46 | 2 |
| 35 | 2 | 47 | 1 |
| 36 | 1 | 48 | 1 |
| 37 | 2 | | |

EXAMPLE 3

Acute toxicity test

Groups of mice, each consisting of 3 to 6 male dd-strain mice having a weight of 20±1 g were orally administered with suspension of some of said compounds in 0.3% CMC solution, and 7 days after the administration lethal states were observed to determine $LD_{50}$.

The results are shown in Table 3.

TABLE 3

| Compound | $LD_{50}$ (mg/kg, P.O.) |
|---|---|
| No. 3 | >300 |
| 7 | >1000 |
| 24 | >300 |
| 9 | >300 |
| 29 | >300 |
| 34 | >300 |

TABLE 3-continued

| Compound | $LD_{50}$ (mg/kg, P.O.) |
|---|---|
| 31 | >300 |
| 33 | >300 |
| 36 | >300 |
| 47 | >300 |

EXAMPLE 4

According to the ordinary procedure, 10,000 tablets having the following composition were prepared, where one tablet contained 50 mg of the effective component.

| | |
|---|---|
| 1-(4-chlorophenyl)-3-methyl-dihydrouracil (compound No. 3) | 500 g |
| Lactose | 343 g |
| Carboxymethylcellulose calcium | 93 g |
| Magnesium stearate | 4 g |
| Talc | 8 g |
| Polyvinyl alcohol | 25 g |
| Glycerine | 2 g |
| Tar pigment | a trace |
| | 975 g |

EXAMPLE 5

According to the ordinary procedure, 10,000 tablets having the following composition were prepared, where one tablet contained 50 mg of the active component.

| | |
|---|---|
| Main chemical (compound No. 7) | 500 g |
| Lactose | 980 g |
| Starch | 520 g |
| Hydroxyprophylcellulose | 80 g |
| Magnesium stearate | 20 g |
| Tar pigment | a trace |
| | 2100 g |

EXAMPLE 6

According to the ordinary procedure, 10,000 tablets having the following composition were prepared, where one tablet contained 50 mg of the active component.

| | |
|---|---|
| Main chemical (compound No. 24) | 500 g |
| Light anhydrous silicic acid | 20 g |
| Crystalline cellulose | 640 g |
| Lactose | 1020 g |
| Magnesium stearate | 20 g |
| Tar pigment | a trace |
| | 2200 g |

REFERENCE EXAMPLE 1

Preparation of 1-(4-chlorophenyl)-3-methyl-dihydrouracil (compound No. 3):

At first, 8 g (0.032 moles) of N-(methylcarbamoyl)-N-(4-chlorophenyl)-β-alanine was added to a mixed solution of 100 ml of 6N hydrochloric acid and 50 ml of acetic acid, and the mixture was refluxed wih heating for two hours. After the completion of reaction, 300 ml of water was added to the reaction mixture. The reaction mixture was left standing in a cold place, and precipitated crystals were recovered therefrom by suction filtration and recrystallized from 70 ml of ethyl acetate and 100 ml of n-hexane, whereby 4.8 g of the desired compound was obtained as crystals having a melting point of 145° to 146° C. (yield: 64.6%).

REFERENCE EXAMPLE 2

Preparation of 3-methyl-1-(3-trifluoromethylphenyl)-dihydrouracil (compound No. 7):

At first, 32 g (0.1 mole) of N-(methylcarbamoyl)-N-(3-trifluoromethylphenyl)-β-alanine was added to a mixed solution of 100 ml of 6N hydrochloric acid and 50 ml of acetic acid, and the mixture was refluxed with heating for two hours. After the completion of reaction, 300 ml of water was added to the reaction mixture. The reaction mixture was left standing in a cold place, and precipitated crystals were recovered therefrom by suction filtration and recrystallized from 70 ml of ethyl acetate and 100 ml of n-hexane, whereby 16.2 g of the desired compound was obtained as crystals having a melting point of 124° to 125° C. (yield: 60.4%).

REFERENCE EXAMPLE 3

Preparation of 3-(2,5-dichlorophenyl)-1-methyldihydrouracil (compound No. 24):

At first, 8.7 g (0.027 moles) of N-(2,5-dichlorophenyl-carbamoyl)-N-methyl-β-alanine was added to 50 ml of thionyl chloride and the mixture was refluxed with heating for one hour. After the completion of reaction, excess thionyl chloride was removed therefrom by distillation under reduced pressure, and then 100 ml of ethyl acetate was added to the residue. The mixture was washed with a saturated aqueous sodium bicarbonate solution twice and then with water, and dried over anhydrous sodium sulfate. After removal of the solvent therefrom by distillation under reduced pressure, precipitated crystals were recrystallized from 100 ml of ethyl acetate and 100 ml of n-hexane, whereby 6.6 g of the desired compound was obtained as crystals having a melting point of 120.5° to 123° C. (yield: 80.9%).

REFERENCE EXAMPLE 4

Preparation of 1-(2-methyl-4-chlorophenyl)-3-methyldihydrouracil (compound No. 9):

At first, 8.0 g (0.03 moles) of N-(2-methyl-4-chlorophenylcarbamoyl)-N-methyl-β-alanine was added to 250 ml of acetic anhydride, and the mixture was refluxed with heating for 2.5 hours. Acetic anhydride was removed therefrom by distillation under reduced pressure, and precipitated crystals were recrystallized from 60 ml of ethyl acetate and 150 ml of n-hexane, whereby 1.8 g of the desired compound was obtained as crystals having a melting point of 120° to 127° C. (yield: 24.1%).

REFERENCE EXAMPLE 5

Preparation of 3-(2-chlorophenyl)-1-methyl-dihydrouracil (compound No. 29):

At first, 8.7 g (0.03 moles) of N-(2-chlophenylcarbamoyl)-N-methyl-β-analine was suspended in 50 ml of ethyl acetate, and 10.7 ml (0.15 moles) of thionyl chloride was added to the suspension. The mixture was stirred at room temperature for 6 hours, and then 50 ml of n-hexane was added thereto. The mixture was left standing in a cold place overnight, and precipitated crystals were recovered therefrom by suction filtration, washed with n-hexane and dried, whereby 6.6 g of the desired compound was obtained as crystals having a melting point of 120.5° to 123° C. (yield: 80.9%).

REFERENCE EXAMPLE 6

Preparation of 1-(2,4-dichlorophenyl)-3-methyldihydrouracil (Compound No. 31):

At first, 7.44 g (0.03 moles) of N-(2,4-dichlorophenyl)-β-alanine methyl ester was dissolved in 150 ml of tetrahydrofuran (THF), and 19.2 ml (0.03 moles) of n-butyl lithium was added thereto at −78° C. Several minutes thereafter, 5.4 ml (0.045 moles) of methyl isocyanate was added thereto. The mixture was stirred at the same temperature for one hour, a saturated aqueous ammonium chloride solution was added thereto, and the mixture was extracted with ethyl acetate. The ethyl acetate layer was washed with water and with a saturated aqueous sodium chloride solution, and dried over anhydrous magnesium sulfate, and the solvent was distilled off under reduced pressure. The residue was subjected to silica gel column chromatography and recrystallized from toluene, whereby 1.32 g of the desired compound was obtained as colorless prism crystals having a melting point of 154°–157° C. (yield: 16.1%).

REFERENCE EXAMPLE 7

Preparation of 3-(2,3-dichlorophenyl)-1-methyldihydrouracil (Compound No. 34):

At first, 7 g (0.032 moles) of N-methoxycarbonyl-2,3-dichloroaniline was dissolved in 150 ml of anhydrous toluene, and 3.84 ml (0.038 moles) of trichlorosilane and 6.6 ml (0.048 moles) of triethylamine were added thereto. The mixture was stirred at 80° C. for one hour.

After excess of trichlorosilane was distilled off under reduced pressure, 3.2 g (0.038 moles) of N-methyl-β-alanine-nitrile was added thereto and the mixture was stirred at room temperature for one hour. Ethyl acetate was added thereto, and the mixture was washed successively with 3N-aqueous hydrochloric acid solution, with water and with a saturated aqueous sodium chloride. The mixture was then dried over anhydrous magnesium sulfate and the solvent was distilled off under reduced pressure. The residue was subjected to silica gel column chromatography and recrystallized from toluene-n-hexane, whereby 4.12 g of N-(2,3-dichlorophenylcarbamoyl)-N-methyl-β-alaninenitrile was obtained as colorless prism cyrstals having a melting point of 97° C. (yield: 47.4%).

Then, 3.5 g (0.013 moles) of the N-(2,3-dichlorophenyl-carbamoyl)-N-methyl-β-alaninenitrile was added to a solution consisting of 30 ml of 6N-hydrochloric acid and 10 ml of acetic acid, and the mixture was refluxed with heating for 4 hours. After completion of the reaction, 50 ml of water was added thereto. The deposited crystals were recovered by filtration with suction and recrystallized from ethyl acetate-n-hexane, whereby 2.43 g of 1-methyl-3-(2,3-dichlorophenyl)-dihydrouracil was obtained as light yellow crystals having a melting point of 163°–165° C. (yield: 69.4%).

REFERENCE EXAMPLE 8

Preparation of 3-methyl-1-(4-trifluoromethylphenyl)-dihydrouracil (Compound No. 33):

At first, 4 g (0.014 moles) of N-(methylcarbamoyl)-N-(4-trifluoromethylphenyl)-β-alanine was added to a solution consisting of 45 ml of 6N-hydrochloric acid and 15 ml of acetic acid, and the mixture was refluxed with heating for 2 hours. After completion of the reaction, 50 ml of water was added thereto. The deposited crystals were recovered by filtration with suction and recrystallized from ethyl acetate-n-hexane, 3.38 g of the desired compound was obtained as colorless needle crystals having a melting point of 115°–117° C. (yield: 90.1%).

REFERENCE EXAMPLE 9

Preparation of 3-(2,4-dichlorophenyl)-1-methyldihydrouracil (Compound No. 36):

In this example, 1.16 g (yield: 15%) of the desired compound as colorless prism crystals having a melting point of 122°–125° C. was obtained from 7 g (0.032 moles) of N-methoxycarbonyl-2,4-dichloroaniline and 4.0 g (0.048 moles) of N-methyl-β-alaninenitrile according to the same manner as in Reference Example 7.

REFERENCE EXAMPLE 10

Preparation of 1-methyl-3-α-naphthyl-dihydrouracil (Compound No. 47):

In this example, 3.75 g (yield: 73.8%) of the desired compound as crystals having a melting point of 228°–229° C. was obtained from 5 g (0.02 moles) of N-(α-naphthylcarbamoyl)-N-methyl-β-alaninenitrile according to the same manner as in Reference Example 8.

What is claimed is:

1. A method for treating convulsion of a mammal which comprises administering to the mammal an effective amount of a composition consisting essentially of a dihydrouracil derivative represented by the formula:

$$\begin{array}{c} X \\ \| \\ B-N \diagdown \diagup N-A \\ O=\!\!\!\diagup \diagdown \\ R_1 \quad R_2 \quad R_3 \end{array}$$

wherein one of A and B is $$\begin{array}{c} Y_1 \\ Y_2 \diagdown \!\!\!\bigcirc \\ Y_3 \end{array}$$

wherein $Y_1$, $Y_2$ and $Y_3$ are hydrogen atoms, lower alkyl groups, halogen atoms, nitro groups, amino groups, carboxyl groups, lower alkoxycarbonyl groups or trifluoromethyl groups, a naphthyl group or a diphenylmethyl group, and the other is a hydrogen atom, a lower alkyl group, a lower alkenyl group, a cyclopentyl group, a cyclohexyl group or $$\begin{array}{c} Z_1 \\ Z_2 \diagdown \!\!\!\bigcirc \\ Z_3 \end{array}$$

wherein $Z_1$, $Z_2$ and $Z_3$ are hydrogen atoms, lower alkyl groups, halogen atoms or trifluoromethyl groups, $R_1$, $R_2$ and $R_3$ are hydrogen atoms or lower alkyl groups, and X is an oxygen atom or a sulfur atom and at least one pharmaceutically acceptable carrier.

2. A method according to claim 1, wherein A is a methyl group, and B is $$\begin{array}{c} Y_1' \\ Y_2 \diagdown \!\!\!\bigcirc \\ Y_3 \end{array}$$

(wherein $Y_1'$ is a halogen atom, a nitro group, an amino group, a trifluoromethyl group or a lower alkoxycarbonyl group, and $Y_2$ and $Y_3$ have the same meanings as defined in claim 1) or a naphthyl group.

3. A method according to claim 2, wherein 1 $Y_2$ and $Y_3$ are hydrogen atoms, or 2 $Y_1'$ is a halogen atom, $Y_2$ is a hydrogen atom and $Y_3$ is a halogen atom at 3-, 4- or 5-position.

4. A method according to claim 1, wherein B is a hydrogen atom or a methyl group, and A is $$\begin{array}{c} Y_1'' \\ Y_2 \diagdown \!\!\!\bigcirc \\ Y_3 \end{array}$$

(wherein $Y_1''$ is a trifluoromethyl group at 3-position, or a halogen atom, an amino group or a trifluoromethyl group at 4-position, and $Y_2$ and $Y_3$ have the same meanings as defined in claim 2.

5. A method according to claim 4, wherein 1 $Y_2$ and $Y_3$ are hydrogen atoms, or 2 $Y_1''$ is a halogen atom at 4-position, $Y_2$ is a hydrogen atom and $Y_3$ is a halogen atom or a methyl group at 2- or 3-position.

6. A method according to claim 1, wherein X is an oxygen atom.

7. A method according to claim 1, wherein $R_1$, $R_2$ and $R_3$ are hydrogen atoms.

8. A method according to claim 1, wherein the effective amount is 100 to 800 mg/60 kg/day of said dihydrouracil derivative.

9. A method according to claim 2, wherein the effective amount is 100 to 800 mg/60 kg/day of said dihydrouracil derivative.

10. A method according to claim 3, wherein the effective amount is 100 to 800 mg/60 kg/day of said dihydrouracil derivative.

11. A method according to claim 4, wherein the effective amount is 100 to 800 mg/60 kg/day of said dihydrouracil derivative.

12. A method according to claim 12, wherein the effective amount is 100 to 800 mg/60 kg/day of said dihydrouracil derivative.

13. A method according to claim 6, wherein the effective amount is 100 to 800 mg/60 kg/day of said dihydrouracil derivative.

14. A method according to claim 7, wherein the effective amount is 100 to 800 mg/60 kg/day of said dihydrouracil derivative.

* * * * *